US009487342B2

(12) United States Patent
Fishman et al.

(10) Patent No.: US 9,487,342 B2
(45) Date of Patent: Nov. 8, 2016

(54) AEROSOL ISOPROPYL ALCOHOL MIXTURE AGENT WITH TRIGGER SPRAYER

(71) Applicants: Michael Scott Fishman, Coral Springs, FL (US); Neal Markus, Hollywood, FL (US)

(72) Inventors: Michael Scott Fishman, Coral Springs, FL (US); Neal Markus, Hollywood, FL (US)

( * ) Notice: Subject to any disclaimer, the term of this patent is extended or adjusted under 35 U.S.C. 154(b) by 82 days.

(21) Appl. No.: 14/305,058

(22) Filed: Jun. 16, 2014

(65) Prior Publication Data

US 2015/0360851 A1    Dec. 17, 2015

(51) Int. Cl.
| B65D 83/14 | (2006.01) |
| B65D 83/20 | (2006.01) |
| B65D 83/22 | (2006.01) |
| B05B 7/24 | (2006.01) |
| A61K 31/045 | (2006.01) |
| A61K 9/12 | (2006.01) |

(52) U.S. Cl.
CPC .......... B65D 83/752 (2013.01); A61K 31/045 (2013.01); B05B 7/2421 (2013.01); B65D 83/201 (2013.01); B65D 83/206 (2013.01); B65D 83/22 (2013.01); B65D 83/226 (2013.01); A61K 9/12 (2013.01)

(58) Field of Classification Search
CPC ............. B05B 1/06; B05B 7/02; B05B 7/04; B05B 7/0416; B05B 7/0441; B05B 7/0483; B05B 7/0815; B05B 7/0838; B05B 7/2402; B05B 7/2405; B05B 7/2416; B05B 7/2421; B05B 9/01; B05B 12/002; B65D 83/206; B65D 83/226; B65D 83/752
See application file for complete search history.

(56) References Cited

U.S. PATENT DOCUMENTS

| 4,175,706 A * | 11/1979 | Gerstmann ........... B05B 7/0416 239/414 |
| 6,056,213 A * | 5/2000 | Ruta ...................... B05B 7/066 239/323 |
| 6,332,563 B2 * | 12/2001 | Baudin ......................... 220/614 |
| 7,621,468 B2 * | 11/2009 | Smith ................... B65D 83/753 222/402.15 |

(Continued)

Primary Examiner — Ryan Reis

(57) ABSTRACT

An Aerosol Isopropyl Alcohol Mixture Agent with Trigger Sprayer that can be easily held in one hand. The Isopropyl Alcohol Mixture Agent is in a bag inside a can and under pressure from air nitrogen, 1,1,1,2-Tetrafluoroethane, Difluoroethane, Petroleum Hydrocarbon, CO2, HFC1234ze, individually or mixture thereof and can only be initially opened and released by pulling the tab of the trigger sprayer. The Trigger Assembly cannot be sprayed until the tab is pulled. The Can is cylindrical canister housing and has a Dip Tube that goes to the bag of the can to the Isopropyl Alcohol Mixture Agent. There is Propellant composed of air nitrogen, 1,1,1,2-Tetrafluoroethane, Difluoroethane, Petroleum Hydrocarbon, CO2, HFC1234ze, individually or mixture thereof in the can that pushes on the bag holding the Isopropyl Alcohol Mixture Agent up through the Dip Tube to the Valve Operative and then to the Actuator Stem up through the Trigger Sprayer Initially pulling the tab of the Trigger Assembly allows the Trigger to be pressed and be moved. Once the Tab is pulled it does not ever need to be pulled again for future uses and allows the Trigger Pivoting Member of the Trigger Assembly to press down on the Actuator Stem which then exerts pressure on the Valve Operative which allows the Propellant in the Can to exert pressure on the bag and force the Isopropyl Alcohol Mixture Agent in the bag through the Dip Tube up the Valve Operative through the Chamber Hole into the Direction Chamber with pressure up through the Nozzle out the Opening toward the area to be treated. The user then holds down the trigger and sprays the area to be treated with the Isopropyl Alcohol Mixture Agent which comes out as a mist in a spray cone.

18 Claims, 8 Drawing Sheets

(56) References Cited

U.S. PATENT DOCUMENTS

2007/0108228 A1* 5/2007 Kleyne ................. A61F 9/00
   222/95
2011/0139810 A1* 6/2011 Lee ....................... B65D 83/44
   222/1
2013/0284824 A1* 10/2013 Morikis ................. A61K 8/39
   239/499

* cited by examiner

AEROSOL ISOPROPYL ALCOHOL MIXTURE AGENT WITH TRIGGER SPRAYER

CROSS-REFERENCE TO RELATED APPLICATIONS

None

FEDERALLY SPONSORED RESEARCH

None

SEQUENCE LISTING

None

BACKGROUND

Traditional way of treating cuts and bruises is the use of a large plastic bottle of Isopropyl Alcohol Mixture Agent pouring it on the wound that can be bulky and cumbersome to use. This invention addresses a new way treating wounds using an aerosol can and trigger sprayer that is both easy to use and fast. The Trigger Sprayer allows the user to be able to pull the tab with their index finger and spray a Isopropyl Alcohol Mixture Agent onto the wound to be treated. Initially when bought there is a tab that needs to be pulled so the Isopropyl Alcohol Mixture Agent is unused and not tampered with until ready to use. When the tab is not pulled the Isopropyl Alcohol Mixture Agent with Trigger sprayer cannot be sprayed. However when the tab is pulled it is opened and can be sprayed when needed. Additionally this invention can easily be held in one hand for ease of use and portability. Finally in emergency situations such as military combat and catastrophes treatment is needed on multiple people at a fast pace so having a trigger sprayer for delivering Isopropyl Alcohol Mixture Agent in a fast a rapid pace would be especially useful. Additionally the spray may be sprayed at any angle and great for all dermatological problems that need a first aid antiseptic.

SUMMARY OF THE INVENTION

The invention is a Isopropyl Alcohol Mixture Agent with a trigger sprayer. In a preferred embodiment of the invention the trigger sprayer is fitted onto a mounting cup with a Valve Operative extending to a dip tube going to the bag inside the aerosol can holding the Isopropyl Alcohol Mixture Agent. The Direction Chamber allows the Isopropyl Alcohol Mixture Agent to flow through the trigger sprayer to the nozzle and out the Opening where it sprays out toward the area or wound to be treated. The Trigger pivots up and down that puts pressure on the Direction Chamber that puts pressure on the actuator stem that exerts pressure on the Valve Operative allowing the Isopropyl Alcohol Mixture Agent to flow up. The Opening on the trigger Assembly can is configured to allow the Isopropyl Alcohol Mixture Agent to flow out as a mist in a spray cone. There is a Propellant composed of nitrogen, air or mixture thereof inside the can that presses on the Bag that holds the Isopropyl Alcohol Mixture Agent. A Mounting Cup is placed in the Hole at the top of the Aerosol Can and holds the pressure of the Propellant and bag containing Isopropyl Alcohol Mixture Agent. The Mounting Cup of the aerosol can has a actuator stem that when it is depressed cause the Valve Operative to allow the Isopropyl Alcohol Mixture Agent pushed up and then to be sprayed out in a conical pattern. The propellant can be Nitrogen, Air or combination of each. The aerosol can is cylindrical. The Trigger sprayer of the aerosol Isopropyl Alcohol has a tab on top of it that can be easily be pulled off which allows the trigger to be depressed and ready to be used. When this tab is not pulled no Isopropyl Alcohol Mixture Agent can come out of the Aerosol Isopropyl Alcohol Mixture with trigger Sprayer for easy storage. The Tab has breakaway hinges and can be snapped off easily. The Trigger can be depressed by an index finger or other fingers to release the Isopropyl Alcohol Mixture Agent. The Trigger Sprayer has a nozzle wherein the Isopropyl Alcohol Mixture Agent can flow be sprayed out in a spray cone with a diameter of 5 and 7 inches at between 4 and 6 inches from the opening of the Nozzle of the Trigger Assembly. The Tigger Assembly having a Trigger for opening and closing the Valve Operative to selectively discharge the Isopropyl Alcohol Mixture Agent from the Opening on the Nozzle as a Mist Spray Cone; wherein the Trigger is operable by pulling the trigger towards the container using one's index finger for opening the Valve Operative and for closing the Valve Operative by releasing the trigger.

Operation of the Invention

When the Tab is not pulled the Trigger of the Aerosol Isopropyl Alcohol Mixture Agent is locked and cannot be sprayed. The operation of the Aerosol Isopropyl Alcohol Mixture Agent with trigger sprayer is when there is a medical emergency and it is needed for use, the user simply pulls the tab of the Aerosol Isopropyl Alcohol Mixture Agent Trigger Sprayer which is located on top and this enables the trigger assembly to be pushed down on the mounting cup that has a stem sticking up that when depressed allows the propellant in the can to exert pressure onto the bag inside the can containing the Isopropyl Alcohol Mixture Agent up through the stem through the Trigger Assembly through the Direction Chamber then up through to the Nozzle and through the opening toward the area to be medically treated. The Isopropyl Alcohol Mixture Agent comes out the opening with pressure in a mist and because the trigger has a nozzle the user can easily identify the direction to spray the Isopropyl Alcohol Mixture Agent.

DETAILED DESCRIPTION

Figure 1:
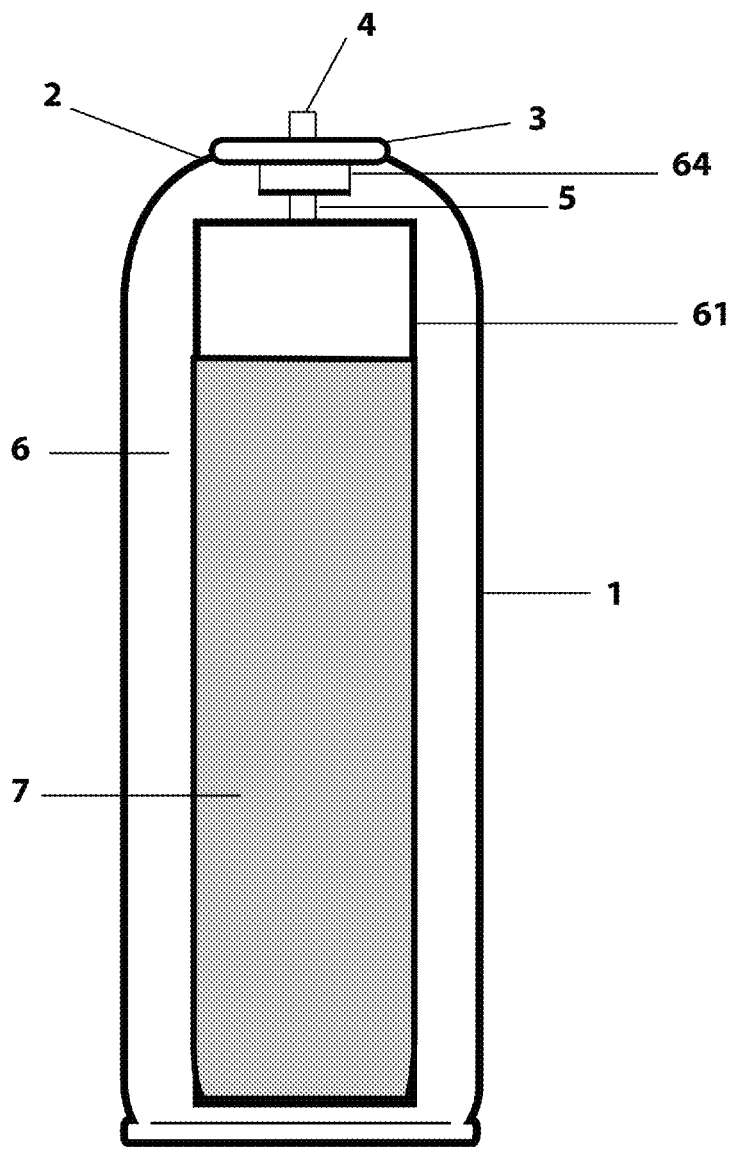
FIG. 1 shows a perspective view of only the Can with the Mounting Cup and Stem with the Bag holding the Isopropyl Alcohol Mixture Agent alone in a preferred embodiment of the invention.

Referring now to FIG. 1, a preferred embodiment of the invention is a Can 1 that is strong enough to withhold aerosol can pressure. The Can 1 has a Can Hole 2 at the top of the can. A Mounting Cup 3 at the top of the can is configured to fit on top of Can 1 into the Can Hole 2. The Mounting Cup 3 has a Actuator Stem 4 which is attached to it and a Valve Operative 64 that configured to attach to a Dip Tube 5 which extends to the Bag 61. The Bag 61 is filled partially with a Isopropyl Alcohol Mixture Agent 7 inside the Can 1. The Can 1 is also filled partially with a Propellant 6.

Figure 2:
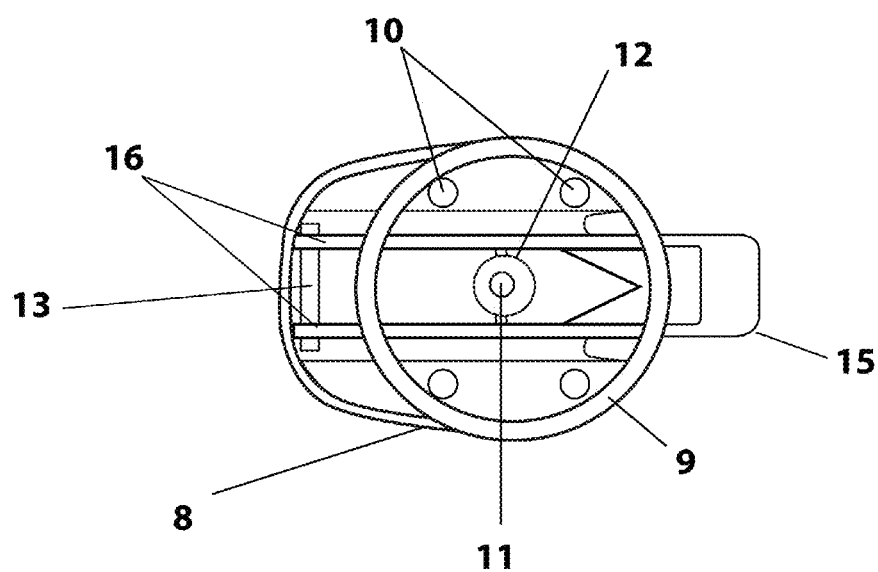
FIG. 2 shows a perspective view of the Trigger Assembly from the bottom of the Trigger Assembly in a preferred embodiment of the invention.

Referring now to FIG. 2 a preferred embodiment of the invention shows the bottom of a Trigger Assembly 8 in a preferred embodiment of the invention. The Trigger Assembly 8 has a Rim 9 configured to snap onto the Mounting Cup 3. The Trigger Assembly 8 also has one or more Fitting Units 10 that are configured to support and to grasp onto the Mounting Cup 3. The Trigger Assembly 8 has a Chamber Hole 11 which secures over the Actuator Stem 4. The Chamber Hole 11 leads into a Direction Chamber 12 and is attached to the back of the Trigger Assembly 8. A Trigger 15 is able to pivot up and down. The Trigger 15 uses a Trigger Pivoting Member 16 to pivot up and down and is held in place by a Trigger Pivoting Member Holder 13.

Figure 3:
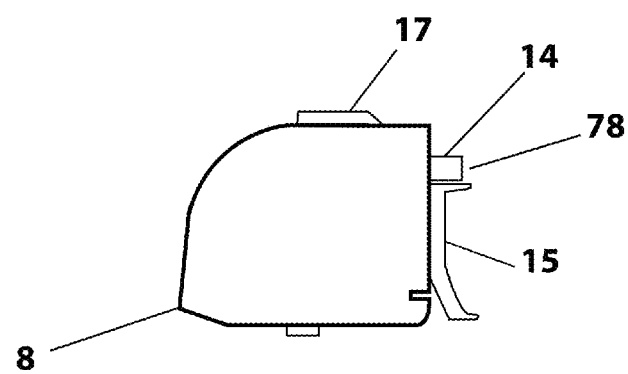
FIG. 3 shows a perspective side view of the Trigger Assembly with the tab intact, FIG. 4 Shows a cross sectional view of the Trigger Assembly with tab intact.

Referring now to FIG. 3 a preferred embodiment of the invention shows a perspective side view of the Trigger Assembly 8. A Tab 17 is fitted on top of the Trigger Assembly 8 which is attached to the Trigger 15 in a preferred embodiment of the invention. The Tab 17 must be removed for the Trigger 15 to move. A Nozzle 14 allows the user to point to where the spray will go. At the end of the Nozzle 14 there is a opening 78 which in the preferred embodiment of the invention has small holes to allow the Isopropyl Alcohol mixture Agent to come out in a mist.

Figure 4:
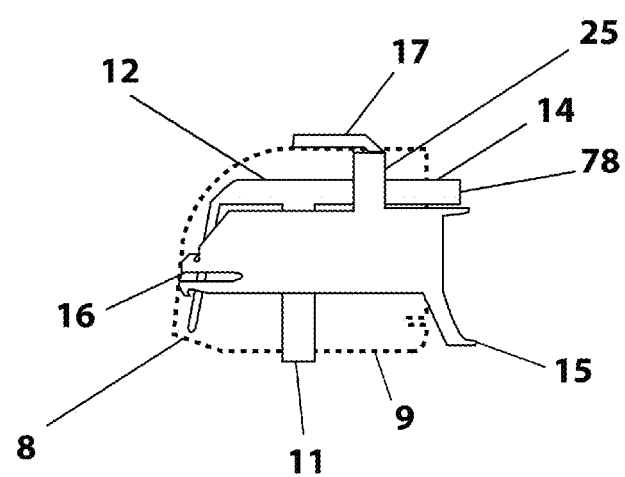
Figure 5:
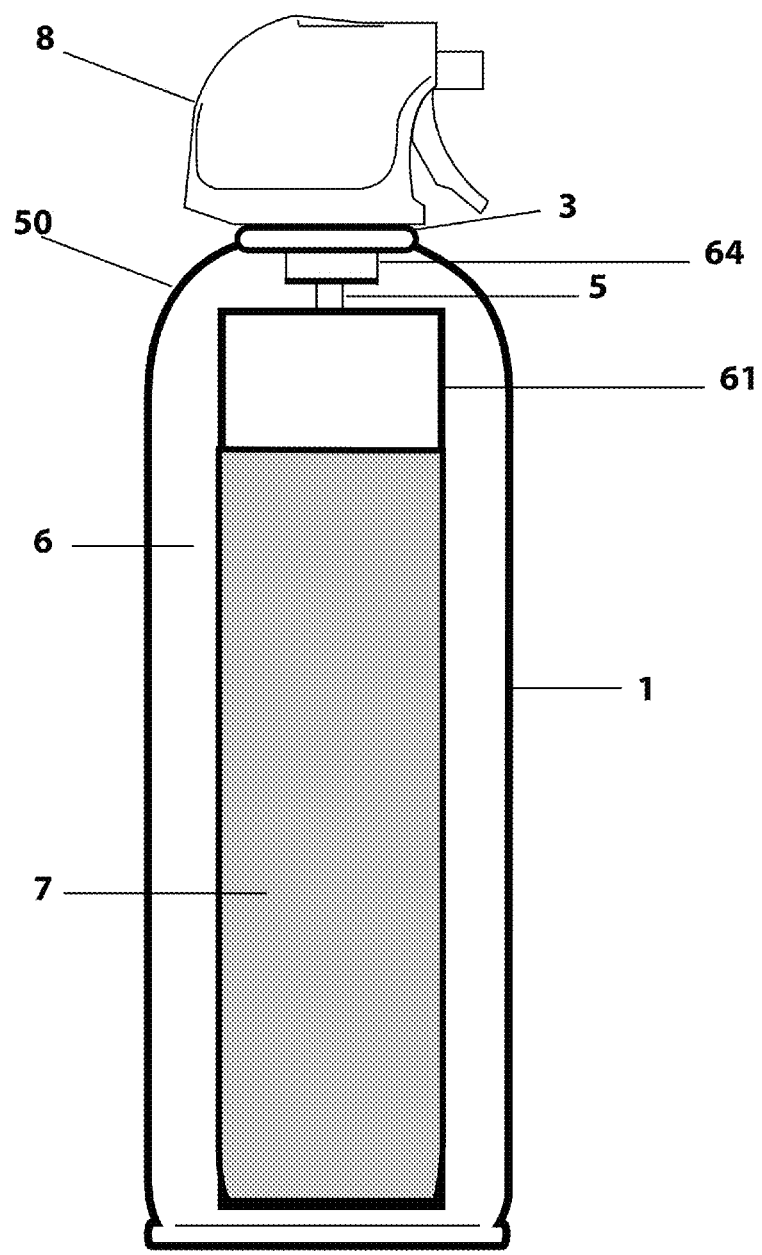
FIG. 5 shows Perspective Cross Sectional view of the Aerosol Isopropyl Alcohol Mixture Agent with a Trigger Assembly and tab intact in a preferred embodiment of the invention.

Referring now to FIG. 4 a cross sectional view of the Trigger Assembly 8. The Chamber Hole 11 is at the bottom and the Rim 9 can be seen that fits over the Mounting Cup 3. A Trigger 15 fits inside the Trigger Assembly 8. The Chamber Hole 11 goes into a Direction Chamber 12 which is hollow and allows the Isopropyl Alcohol Mixture Agent 7 to flow through Chamber Hole 11 into Direction Chamber 12 out a Nozzle 14 in a mist spray pattern. The Trigger 15 Pivots up and down by being pressed by an index finger and by way of its trigger Pivoting Member 16. The Trigger 15 has a Nozzle Holder 25 that holds onto the Nozzle 14. At the end of the nozzle is a Opening 78 with individual small holes to allow the Isopropyl Alcohol Mixture Agent to come out as a mist. Referring now to FIG. 5 which shows a perspective side view of a Isopropyl Alcohol Mixture Agent with Trigger Sprayer. A Isopropyl Alcohol Mixture Agent with Trigger Sprayer Whole Unit 50 is shown as the whole invention. In this perspective view the Can 1 is shown filled with the Isopropyl Alcohol Mixture Agent. The Can 1 is filled with the Propellant 6 composed of nitrogen, air of mixture thereof and the Dip Tube 5 goes to the Bag 61 of the Isopropyl Alcohol Mixture Agent. The Dip Tube 5 then connects to the Valve Operative 64 which is configured to go through the Mounting Cup 3. A Mounting Cup 3 holds the pressure inside the Can 1. The Trigger Assembly 8 fits onto the Mounting Cup 3.

Figure 6:
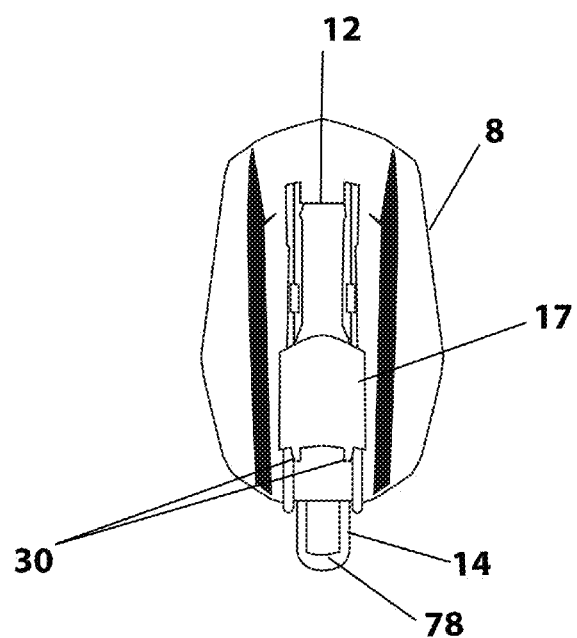
FIG. 6 shows a Perspective view of the Trigger Assembly looking from above.

Referring now to FIG. 6 shows a view of the Trigger Sprayer looking from above. The Tab 17 is shown as it sits on top of the Trigger Assembly 8. In this perspective view the tab has Breakaway Hinges 30 that allows the Tab 17 to be pulled off. When the Tab 17 is pulled off the Nozzle 14 and Direction Chamber 12 are free to move up and down as the Trigger 15 is pressed.

Figure 7:
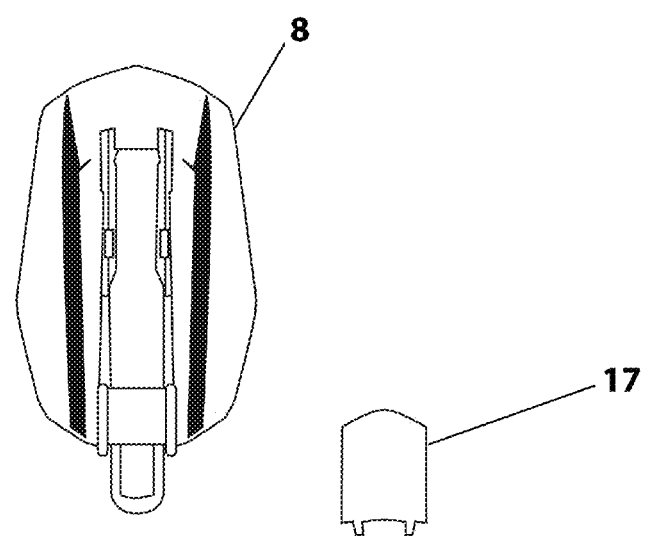
FIG. 7 shows a Perspective view of the Trigger Assembly looking from above with the Tab removed in a preferred embodiment of the invention.

Referring now to FIG. 7 shows a view of the Trigger Sprayer looking from above. The Tab 17 has been pulled for use after initial opening and allowing the Trigger Assembly 8 to be sprayed.

Figure 8:
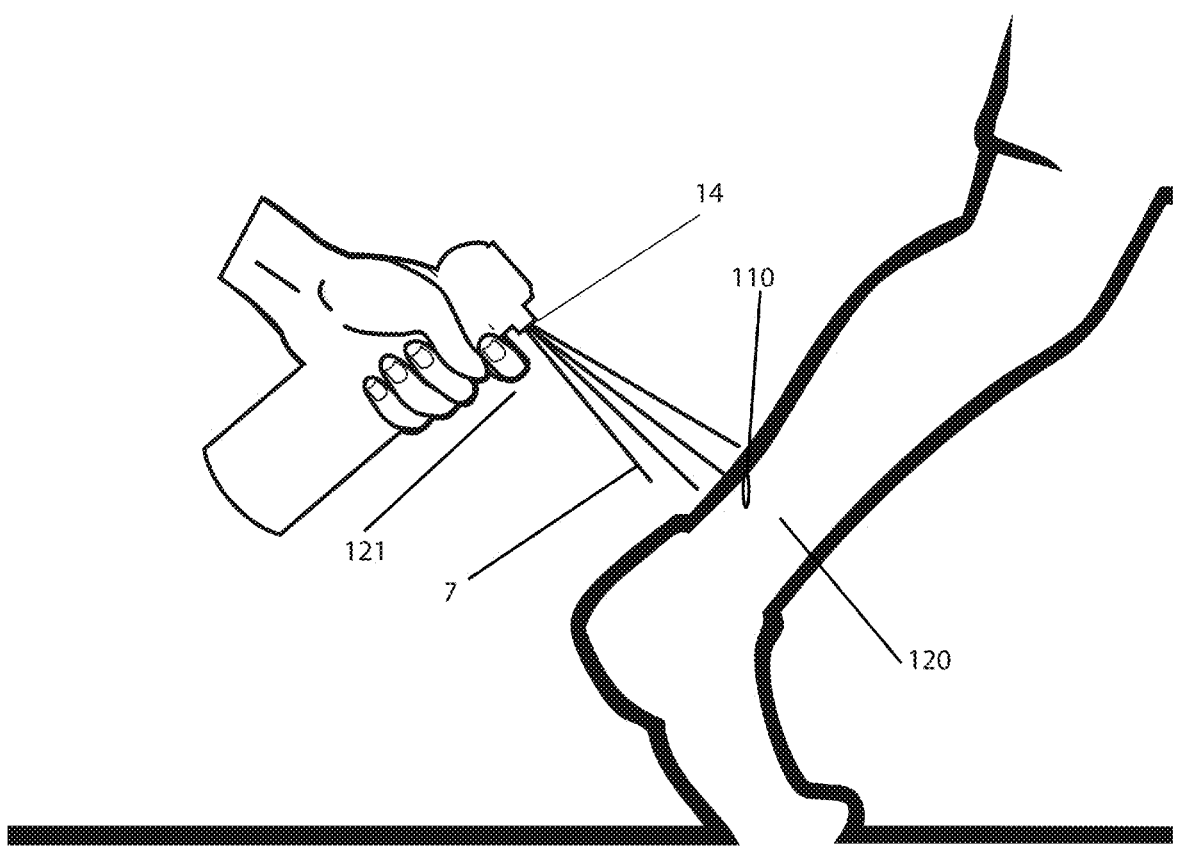
FIG. 8 shows the Perspective side view of the Aerosol Isopropyl Alcohol Mixture Agent with Trigger Assembly being held and used with index finder spraying a conical spray onto the wound of a leg that is being treated.

Referring to FIG. 8 shows a perspective view of a Index Finger 121 squeezing the trigger releasing the Isopropyl Alcohol Mixture Agent 7 through the Nozzle 14 onto a Wound 110 on a Persons Leg 120.

The invention claimed is:

1. An aerosol isopropyl alcohol mixture agent with trigger sprayer comprising:
    (a) a can storing isopropyl alcohol mixture agent in a bag under pressure from a propellant having an opening for discharge for isopropyl alcohol mixture agent there through;
    (b) a valve operative for receiving the isopropyl alcohol mixture agent from the opening;
    (c) a trigger assembly having a nozzle operative for discharging the isopropyl alcohol mixture agent from the can through the valve operative, the trigger assembly having a trigger for opening and closing the valve operative to selectively discharge the isopropyl alcohol mixture agent from the opening of the nozzle as a mist in a spray cone; wherein
    (d) the trigger is operable by pulling the trigger towards the can using one's index finger for opening the valve operative and for closing the valve operative by releasing the trigger; wherein
    (e) the trigger pivots the nozzle about a hinge causing an actuator stem to release pressure causing the isopropyl alcohol mixture agent to flow up into a direction chamber and out the nozzle; and wherein
    (f) the isopropyl alcohol mixture agent comprises between 40-100% isopropyl alcohol and the other percentage is water.

2. An aerosol isopropyl alcohol mixture agent with trigger sprayer comprising:
    (a) a can storing isopropyl alcohol mixture agent in a bag under pressure from a propellant having an opening for discharge for aerosol isopropyl alcohol mixture agent there through;
    (b) a valve operative for receiving the aerosol isopropyl alcohol mixture agent from the opening;
    (c) a trigger assembly having a nozzle operative for discharging the aerosol isopropyl alcohol mixture agent from the can through the valve operative, the trigger assembly having a trigger for opening and closing the valve operative to selectively discharge the aerosol isopropyl alcohol mixture agent from the opening of the nozzle as a mist in a spray cone; wherein
    (d) the trigger is operable by pulling the trigger towards the can using one's index finger for opening the valve operative and for closing the valve operative by releasing the trigger;
    (e) a tab that locks the trigger in place until the first initial use and when pulled off unlocks the trigger for future uses; wherein
    (f) the trigger pivots the nozzle about a hinge causing an actuator stem to release pressure causing the isopropyl alcohol mixture agent to flow up into a direction chamber and out the nozzle; and wherein (g) the isopropyl alcohol mixture agent comprises between 80-98% isopropyl alcohol and the other percentage is water.

3. An aerosol isopropyl alcohol mixture agent with trigger sprayer comprising:
  (a) a can storing isopropyl alcohol mixture agent in a bag, filled under pressure from a propellant made of oxygen having an opening for discharge for isopropyl alcohol mixture agent there through;
  (b) a valve operative for receiving the isopropyl alcohol mixture agent from the opening;
  (c) a trigger assembly having a nozzle operative for discharging the isopropyl alcohol mixture agent from the can through the valve operative, the trigger assembly having a trigger for opening and closing the valve operative to selectively discharge the isopropyl alcohol mixture agent from the opening of the nozzle as a mist in a spray cone; wherein
  (d) the trigger is operable by pulling the trigger towards the can using one's index finger for opening the valve operative and for closing the valve operative by releasing the trigger; wherein
  (e) the trigger pivots the nozzle about a hinge causing an actuator stem to release pressure causing the isopropyl alcohol mixture agent to flow up into a direction chamber and out the nozzle; and wherein
  (f) the isopropyl alcohol mixture agent comprises between 40-79% isopropyl alcohol and the other percentage is water.

4. The invention as recited in claim 1, wherein the propellant comprises nitrogen.

5. The invention as recited in claim 1, wherein the propellant comprises oxygen.

6. The invention as recited in claim 1, wherein the propellant comprises a mixture of oxygen and nitrogen.

7. The invention as recited in claim 1, where in the can holds 1 to 24 fluid ounces.

8. The invention as recited in claim 1, wherein the isopropyl alcohol mixture agent comprises between 40-99% isopropyl alcohol and the other percentage is water.

9. The invention as recited in claim 1, wherein the isopropyl alcohol mixture agent comprises between 40-99% isopropyl alcohol and the water added is distilled, artesian, mineral, public water source, purified, sparkling or spring.

10. The invention as recited in claim 1, wherein the isopropyl alcohol mixture agent comprises 100% isopropyl alcohol.

11. The invention as recited in claim 2, wherein the tab when not removed locks the aerosol isopropyl alcohol mixture agent and prevents it from easily being dispensed for storage and non-tampering on store shelves.

12. The invention as recited in claim 3, wherein the can has a longitudinal axis and the trigger is movable in a direction perpendicular to the longitudinal axis.

13. The invention as recited in claim 1, wherein the can is made of metal such as aluminum or steel, or plastic or a combination thereof.

14. The invention as recited in claim 1, wherein the trigger assembly is made of metal such as aluminum or steel, or plastic or a combination thereof.

15. The invention as recited in claim 1, wherein the aerosol isopropyl alcohol mixture agent with trigger sprayer is a system for healing wounds.

16. The invention as recited in claim 1, wherein the spray cone has a diameter of 5-7 inches at 4-6 inches from the opening of the nozzle of the trigger assembly.

17. The invention as recited in claim 1, wherein the propellant is composed of nitrogen, oxygen, air 1,1,1,2-Tetrafluoroethane, Difluoroethane, Petroleum Hydrocarbon, $CO_2$, HFC1234ze, individually or mixture thereof.

18. The invention as recited in claim 1, further comprising a tab that locks the trigger in place until the first initial use and when pulled off unlocks the trigger for future uses.

\* \* \* \* \*